US006117365A

United States Patent [19]
Ley

[11] Patent Number: 6,117,365
[45] Date of Patent: *Sep. 12, 2000

[54] PHENOLIC ACID AMIDES OF HYDROXY-SUBSTITUTED BENZYLAMINES

[75] Inventor: Jakob Ley, Holzminden, Germany

[73] Assignee: Haarmann & Reimer GmbH, Germany

[*] Notice: This patent issued on a continued prosecution application filed under 37 CFR 1.53(d), and is subject to the twenty year patent term provisions of 35 U.S.C. 154(a)(2).

[21] Appl. No.: 09/141,677

[22] Filed: Aug. 27, 1998

[30] Foreign Application Priority Data

Aug. 27, 1997 [DE] Germany ............................ 197 37 327

[51] Int. Cl.$^7$ .......................... C09K 15/16; C07C 233/05
[52] U.S. Cl. .......................... 252/401; 252/399; 252/404; 426/442; 426/546; 514/617; 564/139; 564/166; 564/167
[58] Field of Search ..................................... 564/139, 166, 564/167; 514/617; 252/399, 401, 404; 426/442, 546

[56] References Cited

FOREIGN PATENT DOCUMENTS

WO 92/20465 11/1992 WIPO .

OTHER PUBLICATIONS

Barrett et al, J.C.S. Perkin I, pp. 652–661, 1979.
Teitel et al, J. Het. Chem., vol. 5, pp 825–829, 1968.
Barry Halliwell, et al., "Free Radicals and Antioxidants in Food and In Vivo: What They Do and How They Work," *Critical Reviews in Food Science and Nutrition*, 35(1&2), 1995, pp. 7–20.
Michael J. Thomas, "The Role of Free Radicals and Antioxidants: How Do We Know That They Are Working?" *Critical Reviews in Food Science and Nutrition*, 35(1&2), 1995, pp. 21–39.
Miles R. Chedekel, "Melanin Can Improve Sunscreens," *Cosmetics & Toiletries® Magazine*, 111, Jan. 1996, pp. 71–74.
Carl–Magnus Anderson, et al., "Advances in the Development of Pharmaceutical Antioxidants," *Advances in Drug Research*, (Eds.) Bernard Testa and Urs A. Meyer, Harcourt Brace & Company, Academic Press, 28, 1996, pp. 67–180.
Halliwell et al., "Free Radicals and Antioxidants in Food and In Vivo: What They Do and How They Work," Critical Reviews in Food Science and Nutrition, vol. 35, (1 and 2), pp. 7–20, (1995).

Andersson et al. "Advances in the Development of Pharmaceutical Antioxidants", Advances in Drug Research, 28:65–180, (1996).
Chedekel, "Melanin Can Improve Sunscreens", Cosmetics & Toiletries, vol. 111, pp. 71–74, (Jan. 1996).
Martin–Tanguy, et al. "The Distribution of Hydroxycinnamic Acid Amides in Flowering Plants", *Biochemistry*, vol. 17, pp. 1927–1928, (1978).
Nakatani et al., "Chemical Constituents of Peppers (Piper spp.) and Application to Food Preservation: Naturally Occurring Antioxidative Compounds", *Environmental Health Perspectives*, vol. 67, pp. 135–142, (1986).
Santos et al., "Grossamide and N–trans–Caffeoyltramine from *Annona crassiflora* Seeds", *Planta Med.* 62, p. 76 (1996).
Negrel et al., "Ether–Linked Ferulic Acid Amides in Natural and Wound Periderms of Potato Tuber", *Phytochemnistry*, vol. 43, No. 6, pp. 1195–1199, (1996).
Burke et al., "Hydroxylated Aromatic Inhibitors of HIV–1 Integrase", *J. Med. Chem.*, vol. 38 pp. 4171–4178, (1995).
Tseng et al., "Inhibition of in VItro Prostaglandin and Leukotriene Biosyntheses by Cinnamoyl–β–phenethylamine and N–Acyldopamine Derivatives", *Chem. Pharm. Bull.*, vol. 40, No. 2, pp. 396–400, (1992).
Muhlenbeck, et al., Formation of Hydroxycinnamoylamides And α–Hydroxyacetovanillone in Cell Cultures of *Solanum Khasianum*, Phytochemistry, vol. 42, No. 6, pp. 1573–1579, (1996).

*Primary Examiner*—Shailendra Kumar
*Attorney, Agent, or Firm*—Brinks Hofer Gilson & Lione

[57] ABSTRACT

The invention relates to specific phenolic acid amides of hydroxy-substituted benzylamines of the formula I (I)

[Chemical structure: phenolic acid amide with substituents $R^1$, $R^2$, $R^3$, $R^4$, $R^5$, $R^6$, $R^7$, $A^1$, showing two phenol rings connected through an amide linkage]

to a process for their preparation and to their use as antioxidants or as free-radical scavengers, in particular in the cosmetic or dermatological field, in foods and cosmetic and dermatological compositions comprising these phenolic acid amides.

24 Claims, No Drawings

PHENOLIC ACID AMIDES OF HYDROXY-SUBSTITUTED BENZYLAMINES

BACKGROUND OF THE INVENTION

1. Field of the Invention

The invention relates to phenolic acid amides of hydroxy-substituted bezylamines, to a process for their preparation and to their use as antioxidants or free-radical scavengers, in particular in cosmetic and pharmaceutical preparations and foods, and for the protection of cells and tissue of mammals against the damaging effect of free radicals and reactive oxygen species which accelerate aging. The invention also relates to cosmetic and pharmaceutical preparations comprising these phenolic acid amides.

2. Discussion of the Background

The autoxidation of lipids, proteins, DNA and other biomolecules is one of the main factors responsible for the aging of physiological systems, including human skin (cf. for example B. Halliwell, M. A. Murcia, S. Chirico, O. I. Aruoma, *Critical Reviews in Food Science and Nutrition*, 1995, 35 (1&2), 7–20 and literature cited therein). It is assumed that the damage of biomolecules and cells by oxidative stress leads to many diseases (cf. M. J. Thomas, *Critical Reviews in Food Science and Nutrition*, 1995, 35 (1&2), 21–39). This is almost certainly the case for some types of cancer. However, also in the case of arthritis and arteriosclerosis a direct connection is suspected.

The skin, as the largest organ in the body and the most important barrier against environmental influences, is particularly affected. For example, primary damage thereto is caused mainly by irradiation or injury. The resulting damage to tissue or cells triggers inter alia processes in which free radicals are produced and/or antioxidants are consumed or promoters of autoxidation are released. In this connection, it is possible, for example, for iron ions or haem to be released, HOCl-producing phagocytes to be activated, the arachidonic acid cascade to be started or also the respiratory chain to be interrupted, in which case reactive oxygen species or free radicals are then released to a greater extent. These could damage lipids in cell membranes, proteins (including intracellular fibrin, enzymes and the intercellular support protein collagen), polysaccharides (e.g. the gel-forming hyaturonic acid) and also the DNA in the cells of the dermis. If this damage is not adequately countered by endogenous processes, the skin ages prematurely. This mainly becomes apparent from a sagging and thus the formation of wrinkles. In addition, cells may go out of control and form tumours, such as, for example, malignant melanomas.

The best known autoxidation is that of lipids, in particular of unsaturated fatty acids, in which in particular the membranes of otherwise intact cells are damaged. The autoxidation proceeds via a free-radical chain mechanism which can be divided into the three steps initiation, propagation and termination (see text books of organic chemistry). The free-radical initiation and propagation are heavily promoted by heavy metal ions, in particular the iron and copper ions present in physiolocial systems.

However, the oxidation of fats or other biomolecules also plays an important role in product protection, for example of cosmetics, pharmaceuticals or foods. In this connection, similar reactions to those described above always take place, the formation of free radicals being initiated in particular by heating, heavy metal ions or UV-light.

It is thus desirable to find substances which, in physiological systems, assist the natural defence mechanisms against free radicals and reactive oxygen species or, as protective substances in cosmetics, pharmaceuticals or foods, protect their oxidation-sensitive constituents against autoxidation.

Antioxidants are defined as substances which, in small concentrations compared to the oxidizable substrate, significantly delay or entirely prevent oxidation. Many antioxidants also function as free-radical scavengers and/or as complexing agents for heavy metal ions.

Some natural and very important antioxidants or free-radical scavengers are the tocopheroles (vitamin E), L-ascorbic acid (vitamin C) and glutathione. In addition, ubiquinone, β-carotene and bilirubin (degradation product of porphyrin derivatives) play a role as antioxidants in vivo (cf. C. -M. Andersson, A. Hallberg, T. Högberg, "Advances in the Development of Pharmaceutical Antioxidants", in *Adv. Drug Res.*, B. Testa, U. A. Meyer (Ed.), Academic Press, London, 1996, p. 65–180). In addition, the polybasic acids, such as, for example, citric acid and amino acids, which have a chelating effect and can thus mask metal ions can also be mentioned. Another antioxidant specific to the skin is melanin formed in melanocytes, a mostly brown-black polymer, which is formed by oxidation and polymerization from aromatic amino acids such as L-tyrosine (cf. M. R. Chedekel, *Cosmetics & Toiletries* 1996, 111(1), 71–74).

The most important non-natural antioxidants, which are used particularly in the food industry for stabilizing fats and oils, are 2- and 3-tert-butyl-4-methoxyphenol (1:9 mixture, butylated hydroxyanisole, BHA) and 2,6-di-tert-butyl-4-methylphenol (butylated hydroxytoluene, BHT), propyl gallate (PG), dodecanyl gallate (DG) and 2-tert-butyl-1,4-dihydroxybenzene (TBHQ). Many of the products formed primarily from free-radical recombinations of phenoxy radicals are themselves also antioxidants. This is one reason why the antioxidants are frequently used as mixtures, since they display a mutual synergistic effect. However, some of these synthetic antioxidants have been classified as unsafe from a toxicological viewpoint (cf. S. M. Barlow, "Toxicological Aspects of Antioxidants Used as Food Additives", in *Food Antioxidants*, B. J. F. Hudson (Ed.), Elsevier, London, 1990, p. 253–307).

Antioxidants which are naturally occurring, particularly in plants, also include, for example, the ω-phenylalkyl acid derivatives, such as p-coumaric acid, caffeic acid, ferulic acid, sinapic acid and analogues and also some flavonoids.

Some ferulic acid amides of hydroxy-substituted 2-(phenyl-)-ethylamines (Martin-Tanguy, J.; Cabanne, F.; Pedrizet, E.; Martin, C., *Phytochemistry* 1978, 17 (11), 1927–1928) can also be found in nature; of these compounds, N-2-(4-hydroxyphenyl)ethyl-4-hydroxy-3-methoxy-E-cinnamamide, in particular, have been found in a large number of plants, such as, for example, in the tomato. The compound has also been isolated from black pepper, and the antioxidative effect has been described (JP 57,146,563; Nakatani, N.; Inatani, R.; Ohta, H.; Nishioka, A., *EHP, Envir. Health Perspect.* 1986, 67, 135–142). However, the compound is only present in small amounts in the plants (0.03%) and is not available in adequate amounts. In addition, as we have been able to establish, its action is no better than α-tocopherol (cf. Experiments 2 and 2).

A few other ferulic acid amides and caffeic acid amides of phenethylamines have been isolated from a variety of plants such as, for example, N-2-(4-hydroxyphenyl)ethyl-3,4-dihydroxy-E-cinnamamide from horse chestnuts (Martin-Tanguy, J.; Cabanne, F.; Pedrizet, E.; Martin, C., *Phytochemistry* 1978, 17 (11), 1927–1928) or from *Annona*

*crassiflora* Mart. (Santos, L. P.; Boaventura, M. A. D.; de Oliveira, A. B.; Cassady, J. M., *Planta Medica* 1996, 62 (1), 76–77). In the case of some plants, particularly in the case of Solanaceae, they are formed as a response to an injury (example: N-2-(4-hydroxyphenyl)-2-hydroxyethyl-4-hydroxy-3-methoxy-E-cinnamamide in the potato: Negrel, J.; Pollet, B.; Lapierre, C., *Phytochernistry* 1996, 43 (6), 1195–1199).

The action of some N-hydroxycinnamoylhydroxyanthranilic acids, which are present inter alia in oats, as insecticides is described, for example, in NL 92,02,078.

Some polyhydroxylated dihydrocinnamamides of 2-(phenyl)ethylamines have been described in the literature, for example N-2-(3,4-dihydroxyphenyl)ethyl-3-(3,4-dihydroxyphenyl)propanamide as an HIV-integrase inhibitor (Burke, T. R.; Fresen, M. R.; Mazumder, A.; Wang, J.; Carothers, A. M.; Grunberger, D.; Driscol, J.; Kohn, K.; Pommier, Y., *J. Med. Chem.*, 1995, 38 (21), 4171–4178).

N-(4-hydroxy-3-methoxybenzyl)-4-hydroxy-3-methoxyphenylacetamide and its N-methyl derivative have been described as antiallergic active ingredients (WO 92 20,645).

At least the abovementioned phenolic acid amides occurring in nature have hitherto only been isolated or synthesized in small amounts and are thus available only in insufficient quantities.

The literature has not yet described any generally applicable and satisfactory processes for the synthesis of the aforementioned compounds. The classical coupling of the acid chlorides with amines frequently fails because of secondary reactions, in particular self-condensation of the phenolic acids, which cannot be completely suppressed even by using O-acetyl protective groups, and gives low yields (<35%, cf. Tseng, C .F.; Iwakami, S.; Mikajiri, A.; Shibuya, M.; Hanaoka, F.; Ebizuka, Y.; Padmawinata, K.; Sankawa, U., *Chem. Pharm. Bull.* 1992, 40, 396–400).

A synthesis of some ferulic acid and caffeic acid tyramides by aminolysis of the N-hydroxysuccinimidyl ester for analytical purposes has been described in the literature (cf. Mühlenbeck, U.; Kortenbusch, A.; Barz, W., *Phytochemistry* 1996, 42,1573–1579). However, no details of yields were given.

SUMMARY OF THE INVENTION

The object of the present invention, building on the above knowledge, is to develop novel antioxidants having a strong specific free-radical-scavenging and antioxidative effect, the aim being for the molecules to have a molecular mass below 400 Da and to be readily accessible by synthetic methods.

DESCRIPTION OF THE INVENTION

The invention relates to phenolic acid amides of hydroxy-substituted benzylamines of the general formula I

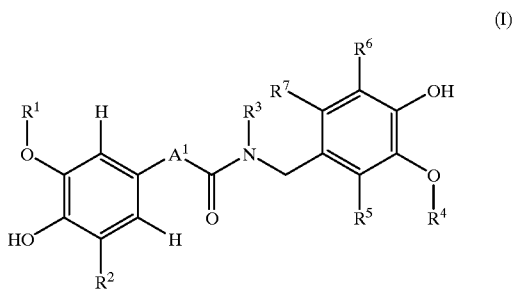

(I)

in which
A$^1$ is a —CH$_2$— group, a —CH$_2$—CH$_2$— group or a —CH=CH— group, it being possible for the last-named group to be either in the (Z)-configuration or in the (E)-configuration, and R$^1$ is a hydrogen atom or an alkyl radical having from 1 to 4 carbon atoms, and R$^2$ is a hydrogen atom or an —O—R$^8$ group, in which R$^8$ is a hydrogen atom or an alkyl radical having from 1 to 4 carbon atoms, and R$^3$ is a hydrogen atom, an acyl, alkyl or alkenyl radical having from 1 to 22 carbon atoms or a —(CH$_2$—CH$_2$—O—)$_n$H group, where n can be from 1 to 15, and R$^4$ is a hydrogen atom or an alkyl radical having from 1 to 4 carbon atoms, with the proviso that at least one of the two radicals R$^1$ and R$^4$ is a hydrogen atom, and R$^5$, R$^6$ and R$^7$ independently of one another are hydrogen atoms or —O—R$^9$ groups, in which R$^9$ is a hydrogen atom or an alkyl radical having from 1 to 4 carbon atoms.

Preference is given to compounds of the general formula I, in which
A$^1$ is a —CH$_2$— group, a —CH$_2$—CH$_2$— group or a —CH=CH—group in the (E)-configuration, and R$^1$ is a hydrogen atom or a methyl group, and R$^2$ is a hydrogen atom, a hydroxyl group or an —O—CH$_3$ group, and R$^3$ is a hydrogen atom, alkyl or alkenyl radical having from 1 to 22 carbon atoms or a —(CH$_2$—CH$_2$—O—)$_n$H group, where n is from 1 to 15, and R$^4$ is a hydrogen atom or a methyl group, with the proviso that at least one of the two radicals R$^1$ and R$^4$ is a hydrogen atom, and R$^5$, R$^6$ and R$^7$ independently of one another are hydrogen atoms, hydroxyl groups or —O—CH$_3$ groups.

Examples of particularly preferred compounds of the general formula (I) include:
N-(3,4-dihydroxybenzyl)-4-hydroxy-3 -methoxy-E-cinnamamide,
N-(3,4-dihydroxybenzyl)-3,5 -dimethoxy-4-hydroxy-E-cinnamamide,
N-(2,3,4-trihydroxybenzyl)-4-hydroxy-3 -methoxy-E-cinnamamide,
N-(2,3,4-trihydroxybenzyl)-3, 5-dimethoxy-4-hydroxy-E-cinnamamide,
N-(3,4,5-trihydroxybenzyl)-4-hydroxy-3 -methoxy-E-cinnamide,
N-(3,4-dihydroxybenzyl)-4-hydroxy-3 -methoxyphenylacetamide,
N-(3,4-dihydroxybenzyl)-3 -(4-hydroxy-3 -methoxyphenyl)-propanamide, N-(4-hydroxy-3-methoxybenzyl)-3-(3,4-dihydroxyphenyl)-propanamide, N-(3,4-dihydroxybenzyl)-3-(3,4-dihydroxyphenyl)-propanamide, N-(2,3,4-trihydroxybenzyl)-3-(3,4-dihydroxyphenyl)-propanamide, N-(3,4-dihydroxybenzyl)-3,4-dihydroxy-E-cinnamamide, N-(4-hydroxy-3-methoxybenzyl)-3,4-dihydroxy-E-cinnamamide, N-(3,5-dimethoxy-4-hydroxy-benzyl)-3,4-dihydroxy-E-cinnamamide, N-(2,3,4-trihydroxybenzyl)-3,4-dihydroxy-E-cinnamamide, N-(4-hydroxy-3-methoxybenzyl)-3,4-dihydroxyphenylacetamide and N-(3,4-dihydroxybenzyl)-3,4-dihydroxyphenylacetamide, but are not limited thereto.

Surprisingly, we have now found that the novel phenolic acid amides of hydroxy-substituted benzylamines are particularly strong free-radical scavengers and strong antioxidants. In particular, they are significantly better antioxidants and free-radical scavengers than the naturally occurring hydroxycinnamamides of 2-(phenyl)ethylamines (see above) and most of the customary antioxidants (see experiments).

For the purposes of the invention, particularly advantageous antioxidants or free-radical scavengers are compounds having more than three hydroxyl groups. The novel phenolic acid amides of hydroxy-substituted benzylamines of the general formula I can be prepared by the customary amide synthesis processes known per se, which involve reacting an activated phenolic acid, which is optionally protected on the phenolic OH groups, with a benzylamine which is optionally protected on the phenolic OH groups or its ammonium salt, optionally in the presence of the solvents and auxiliary bases. Activated acid derivatives which may be used are the acid chlorides, acid anhydrides or acid esters of, for example, optionally substituted phenols, N-hydroxysuccinimide or N-hydroxybenzotriazole. Preferred protective groups are acyl, carbamate or ether groups, for example acetyl, benzoyl, methoxycarbonyl, tert-butoxycarbonyl, allyl or benzyl groups. Examples of solvents which may be used are water, acetone, dioxane, dimethylformamide, tetrahydrofuran, ethyl acetate, chloroform and also mixtures of the last-named solvents. Examples of auxiliary bases which may be used are the carbonates, hydrogencarbonates and hydroxides of ammonium, alkali metals or alkaline earth metals, and tertiary amines.

The novel phenolic acid amides of hydroxy-substituted benzylamines of the general formula I are particularly preferably prepared from phenolic acid N-succinimidyl esters, which are optionally blocked on the hydroxyl groups with acetyl or methoxycarbonyl groups, and a hydroxy-substituted benzylamine or its ammonium salt in a hydrous solvent mixture, preferably a water/1,4-dioxane mixture with one of the abovementioned auxiliary bases at from 5 to 100° C.

The activated N-succinimidylesters of phenolic acids used are, in particular, N-succinimidyl 4-hydroxy-3-methoxy-E-cinnamate, N-succinimidyl 3,5-dimethoxy-4-hydroxy-E-cinnamate, N-succinimidyl 3,4-bis(acetyloxy)-E-cinnamate, N-succinimidyl 3,4-bis(methoxycarbonyloxy)-E-cinnamate, N-succinimidyl 4-hydroxy-3-methoxyphenylacetate, N-succinimidyl 3,4-bis(methoxycarbonyloxy)-phenylacetate, N-succinimidyl 3-(4-hydroxy-3-methoxyphenyl)-propanoate and N-succinimidyl 3-(3,4-dihydroxyphenyl)-propanoate.

The hydroxy-substituted benzylamines used are, in particular, 3,4-dihydroxybenzylamine, 4-hydroxy-3-methoxybenzylamine, 3,4-dimethoxy-4-hydroxybenzylamine, 2,3,4-trihydroxybenzylamine or 3,4,5-trihydroxybenzylamine or the corresponding ammonium salts.

The novel phenolic acid amides can, however, also be obtained by direct condensation of the free acids with the free amines with or without solvent. Examples of condensing agents which may be used are carboduimides, preferably N,N'-dicyclohexylcarbodiimide, and examples of solvents which may be used are 1,4-dioxane, tetrahydrofuran, tert-butyl methyl ether or ethyl acetate.

The novel phenolic acid amides are obtained from these reaction mixtures by purification steps which are well known to the person skilled in the art; where appropriate, any protective groups still present must be cleaved off using methods known per se.

The novel phenolic acid amides of hydroxy-substituted benzylamines of the general formula I can be used as antioxidants or free-radical scavengers to protect against oxidation and photooxidation. Preferably, they can be used in cosmetic, pharmaceutical or dermatological formulations or in foods. The novel phenolic acid amides are particularly preferably used in cosmetic or dermatological formulations which have the customary composition and are used for the treatment, care and cleansing of skin and/or hair and used as makeup products in decorative cosmetics.

Accordingly, the present invention also relates to cosmetic and pharmaceutical compositions, in particular cosmetic and dermatological compositions which comprise the novel phenolic acid amides in an effective amount, in addition to other otherwise customary composition constituents. They comprise from 0.0001% by weight to 30% by weight, preferably from 0.0001 to 20% by weight, but in particular from 0.0001% by weight to 5% by weight, based on the total weight of the formulation, of the novel phenolic acid amides of the general formula I and can either be in the form of water-in-oil or oil-in-water emulsions. Further customary cosmetic auxiliaries and additives may be present in amounts of 5–95% by weight, preferably 10–80% by weight, based on the total weight of the formulation. In addition, the formulations may include water in an amount up to 99% by weight, preferably 5–80% by weight, based on the total weight of the formulation.

For use, the novel cosmetic and dermatological preparations are applied to the skin and/or the hair in a sufficient amount in the manner customary for cosmetics.

The novel cosmetic and dermatological preparations may comprise cosmetic auxiliaries and additives, as are customarily used in such preparations, for example preservative, bactericides, fungicides, perfumes, antifoams, dyes, pigments which have a colouring effect, thickeners, surfactants, emulsifiers, emmolients, moisturizers and/or humectants, fats, oils, waxes and other customary constituents of a cosmetic or dermatological formulation, such as alcohols, polyols, polymers, foam stabilizers, electrolytes, organic solvents or silicone derivatives.

The novel phenolic acid amides of hydroxy-substituted benzylamines can preferably be combined either with one another or with other antioxidants. In particular, the novel phenolic acid amides of hydroxy-substituted benzylamines can be combined with one another or with tocopherols (vitamin E), tocopherol derivatives, tocotrienols, ascorbic acid (vitamin C), ascorbic acid derivatives, carotinoids, vitamin A or its derivatives, BHT, BHA, gallic esters, flavonoids such as, for example, quercetin or myricetin, catechins such as, for example, epicatechin, epicatechin gallate, epigallocatechin or epigallocatechin gallate, thiols such as, for example, glutathione or other customary antioxidants.

The amount of the aforementioned typical antioxidants (one or more compounds), which are not identical to novel phenolic acid amides of hydroxy-substituted benzylamines, in the novel preparations can amount to from 0.0001 to 30% by weight, preferably from 0.0001 to 20% by weight, particularly preferably from 0.0001 to 5% by weight, based on the total weight of the preparation.

The novel phenolic acid amides of hydroxy-substituted benzylamines can, however, also be used together with UVA and/or UVB filter substances in the novel cosmetic or dermatological formulations, it being possible for the total amount of filter substances to amount to from 0.1 to 30% by weight, preferably from 0.5% to 10% by weight, based on the total weight of the preparations, in which case suncreens for skin and hair are obtained.

Finally, for the purposes of the invention, in a preferred embodiment, the phenolic acid amides of hydroxy-substituted benzylamines can also be dissolved in squalene or squalane and formulated, optionally with the other ingredients together with volatile or nonvolatile silicone compounds, as non-aqueous or virtually non-aqueous systems.

An advantageous embodiment of the present invention is the use of novel phenolic acid amides of hydroxy-substituted benzylamines for the protection of tissue and cells of mammals, in particular the skin and/or the hair, against oxidative stress and the harmful effect of free radicals.

The present invention likewise also relates to a process for protecting cosmetic or dermatological preparations against oxidation or photooxidation, these preparations being, for example, preparations for the treatment and care of skin or hair or also makeup products, the constituents of which are subject to stability problems due to oxidation or photooxidation during storage, characterized in that the cosmetic or dermatological preparations have an effective content of novel phenolic acid amides of hydroxy-substituted benzylamines.

The novel phenolic acid amides of hydroxy-substituted benzylamines can thus also be used for the preparation of pharmaceutical, in particular dermatological, compositions for the protection of cells and tissue of mammals, in particular of humans, against the harmful effect of free radicals and reactive oxygen species.

The amount of novel phenolic acid amides of hydroxy-substituted benzylamines in these preparations is from 0.0001% by weight to 30% by weight, preferably from 0.0001 to 20% by weight, particularly preferably from 0.0001% by weight to 5% by weight, based on the total weight of the preparations.

The present invention also relates to the use of the novel phenolic acid amides for the protection of foods, preferably foods containing fats or fatty derivatives such as, for example, fatty acids or fatty alcohols, but in particular foods which contain fats or fatty acid derivatives having oxidizable double bonds, against oxidative stress and the harmful effect of free radicals.

The amount of novel phenolic acid amides in foods is preferably from 0.0001% by weight to 30% by weight, particularly preferably from 0.0001 to 20% by weight, but in particular from 0.0001% by weight to 5% by weight, based on the total weight of the food.

For the novel use for the protection of foods, the novel phenolic acid amides can preferably be combined with one another or with other antioxidants, examples of which are listed above.

The amount of the abovementioned typical antioxidants (one or more compounds), which are not identical to novel phenolic acid amides, in foods is preferably from 0.0001 to 30% by weight, particularly preferably from 0.0001 to 20% by weight, in particular from 0.0001 to 5% by weight, based on the total weight of the foods.

EXAMPLES

The examples below serve to illustrate the present invention without limiting it.

N-(3,4-Dihydroxybenzyl)-4-hydroxy-3-methoxy-E-cinnamamide (1)

N-succinimidyl ferulate (503 mg, 1.73 mmol) and 3,4-dihydroxybenzylamine hydrobromide (402 mg, 1.83 mmol) were dissolved in water (10 ml) and 1,4-dioxane (10 ml) under nitrogen. After $NaHCO_3$ (160 mg, 1.90 mmol) had been added, the solution was stirred for 2.5–3 h at about 70° C. and left to cool. The mixture was extracted with ethyl acetate, the combined organic phases were washed with hydrochloric acid (10%), water and saturated aqueous NaCl solution, dried over $Na_2SO_4$ and filtered, and the filtrate was evaporated under reduced pressure and the residue was purified by chromatography on silica gel. Yield: 540 mg (99%); $^1$H-NMR (400MHz, $CDCl_3$): $\delta$=7.55 (1H, d, 15.5 Hz), 7.02 (1H, dd, 8.2 Hz, 1.9 Hz), 6.93 (1H, s, 1.9 Hz), 6.89 (1H, d, 8.3 Hz), 6.88 (1H, d, 2Hz), 6.82 (1H, d, 8.1 Hz), 8.72 (1H, dd, 8.1 Hz, 2.0 Hz), 6.51 (1H, s), 6.21 (1H, d, 15.5 Hz), 5.82 (1H, t, 5.8 Hz) 5.79 (1H, s), 5.45 (1H, s), 4.45 (2H, d, 5.8 Hz), 3.90 (3H, s) ppm; $^{13}$C-NMR (100 MHz, $CDCl_3$): $\delta$=165.1, 148.2, 147.8, 145.1, 144.1, 139.0, 130.3, 126.4, 121.4, 119.0, 118.3, 115.6, 115.3, 115.0, 110.8, 55.5, 41.9 ppm, MS (EI): m/z=315.1 (100%), 178.1 (66%), 177.1 (84%), 150.1 (36%), 147.0 (22%), 145.1 (46%), 138.1 (83%), 117.1 (24%), 89.0 (24%), 77.1 (22%).

Using an analogous method, the following compounds were obtained in the form of colourless or slightly yellowish crystals or amorphous solids:

N-(3,4-Dihydroxybenzyl)-3,5-dimethoxy-4-hydroxy-E-cinnamamide (2)

$^1$H-NMR (400 MHz, $CD_3OD$): $\delta$=7.46 (1H, d, 15.6 Hz), 6.85 (2H, s), 6.75 (1H, d, 2.1 Hz), 6.72 (1H, d, 8.1 Hz), 6.64 (1H, dd, 8.1 Hz, 2.0 Hz), 6.47 (1H, d, 15.6 Hz), 4.33 (2H, s), 3.86 (6H, s) ppm; $^{13}$C-NMR (100 MHz, $CD_3OD$): $\delta$=168.8 (s), 149.5 (d), 146.5 (s), 145.7 (s), 142.5 (2*s), 139.0 (s), 131.4 (s), 127.3 (s), 120.3 (d), 119.2 (d), 116.3 (d), 116.0 (d), 106.5 (2*d), 56.8 (2*q), 44.1 (t) ppm, MS (EI): m/z=345.1 (43%), 209.2 (13%), 208.1 (100%), 207.1 (20%), 180.1 (43%), 177.1 (21%), 175.1 (13%), 165.1 (16%), 138.1 (37%), 123.1 (16%).

N-(2,3,4-Trihydroxybenzyl)-4-hydroxy-3-methoxy-E-cinnamamide (3)

$^1$H-NMR (400 MHz, $CD_3OD$): $\delta$=7.47 (1H, d, 14.5 Hz), 7.11 (1H, d,≈2 Hz), 7.03 (1H, dd, 8 Hz,≈2 Hz), 6.77 (1H, d, 8 Hz), 6.53 (1H, d, 8 Hz), 6.41 (1H, d, 14.5 Hz), 6.34 (1H, d, 8 Hz), 4.33 (2H, s), 3.86 (3H, s) ppm; MS (ESI pos.) m/z=332.1 (100%, $[M+H]^+$), 333.0 (20%, $[M+2H]^+$).

N-(2,3,4-Trihydroxybenzyl)-3,5-dimethoxy-4-hydroxy-E-cinnamamide (4)

$^1$H-NMR (400 MHz, $CD_3OD$): $\delta$=7.46 (1H, d, 14 Hz), 6.85 (2H, s), 6.55 (1H, d, 9 Hz), 6.45 (1H, d, 14 Hz), 6.32 (1H, d, 9 Hz), 4.33 (2 H, s), 3.87 (6H, s); MS (ESI pos.) m/z=362.0 (100%, $[M+H]^+$), 362.9 (20%, $[M+2H]^+$).

N-(3,4,5-Trihydroxybenzyl)-4-hydroxy-3-methoxy-E-cinnamamide (5)

$^1$H-NMR (400 Mhz, CDCl$_3$): δ=7.46 (1H, d, 15 Hz), 7.12(1H, d, 2 Hz), 7.03 (1H, dd, 8.5 Hz, 2 HZ), 6.78 (1H, d, 8.5 Hz), 6.45 (1H, d, 15 Hz), 6.32, (2H, s), 3.88 (3H, s) ppm; MS (APCl-)m/z=660.8 (100%, [2M-H], 330.1 (99.9%, [M-H]).

N-(3,4-Dihydroxybenzyl)-4-hydroxy-3-methoxyphenylacetamide (6)

$^1$H-NMR (400 MHz, CDCl$_3$): δ=6.84 (1H, d, 1.7 Hz), 6.72 (1H, d, 7.9 Hz), ca. 6.70 (2H, m), 6.68 (1H, d, 8.0 Hz), 6.56 (1H, dd, 8.0 Hz, 2.1 Hz), 4.20 (2H, s), 3.80 (3H, s), 3.42 (2H, s) ppm; $^{13}$C-NMR (100 MHz, CDCl$_3$): δ=174.3 (s), 149.0 (s), 146.6 (s), 131.4 (s), 128.3 (s), 122.8 (d), 120.2 (d), 116.2 (2*d), 116.1 (d), 113.6 (d), 56.4 (q), 44.1 (t), 43.5 (t) ppm; MS (EI): m/z=303 (41%), 138 (48%), 137 (100%), 123 (76%), 122 (14%), 94 (10%), 77 (13%).

N-(3,4-Dihydroxybenzyl)-3-(4-hydroxy-3-methoxyphenyl)-propanamide (7)

$^1$H-NMR (400 MHz, CD$_3$OD): δ=6.76 (1H, d, 2.0 Hz), 6.69–6.61 (4H, m), 6.45 (1H, dd, 2.1 Hz, 8.0 Hz), 4.16 (2H, s), 3.78 (3H, s), 2.84 (2H, m), 2.46 (2H, m) ppm; $^3$C-NMR (100 MHz, CD$_3$OD): δ=175.1 (s), 148.9 (s), 146.4 (s), 145.9 (s), 145.6 (s), 133.7 (s), 131.3 (s), 121.9 (d), 120.1 (d), 116.3 (d), 117.0 (d), 116.0 (d), 113.2 (d), 56.4 (q), 43.9 (t), 39.4 (t), 32.6 (t) ppm; MS (APCl+): m/z=318.0 (100%, [M+H]$^+$), 634.7 (40%, [2M+H]$^+$).

N-(4-Hydroxy-3-methoxybenzyl)-3-(3,4-dihydroxyphenyl)-proyanamide (8)

$^1$H-NMR (400 MHz, CD$_3$OD): δ=6.76 (1H, d, 2.0 Hz), 6.70 (1H, d, 8.1 Hz), 6.64 (1H, d, 8.1 Hz), 6.64 (1H, d, 2.1 Hz), 6.58 (1H, dd, 81, Hz, 2.0 Hz), 6.50 (1H, dd, 8.1 Hz, 2.1 Hz), 4.22 (2H, s), 3.79 (3H, s), 2.77 (2H, m), 2.45 (2H, m) ppm; $^{13}$C-NMR (100 MHz, CD$_3$OD): δ=175.2 (s), 149.0 (s), 146.8 (s), 146.3 (s), 144.7 (s), 133.7 (s), 131.3 (s), 121.4 (d), 120.6 (d), 116.6 (d), 116.3 (d), 116.1 (d), 112.4 (d), 56.4 (q), 44.1 (t), 39.3 (t), 32.4 (t) ppm; MS (APCl+): m/z=317.9 (100%, [M+H]$^+$), 635.0 (45%, [2M+H]$^+$).

N-(3,4-Dihydroxybenzyl)-3-(3,4-dihydroxyphenyl)-propanamide (9)

$^1$H-NMR (400 MHz, CD$_3$OD): δ=6.68 (1H, d, 8.1 Hz), 6.67 (1H, d, 2.0 Hz), 6.65 (1H, d, 8.1 Hz), 6.64 (1H, d, 2.1 Hz), 6.51 (1H, dd, 8.1 Hz, 2.1 Hz), 6.48 (1H, dd, 8,1 Hz, 2.1 Hz), 4.16 (2H, s), 2.77 (2H, m), 2.43 (2H, m) ppm; $^{13}$C-NMR (100 MHz, CD$_3$OD): δ=175.2 (s), 146.3 (s), 146.2 (s), 145.6 (d), 144.6 (s), 133.8 (s), 131.4 (s), 120.7 (d), 120.2 (d), 116.6 (d), 116.4 (d), 116.3 (d), 116.0 (d), 43.9 (t), 39.5 (t), 32.5 (t) ppm; MS (ESI-): m/z=302.3 (100%, [M–H]$^-$), 605.0 (35%, [2M–H]$^-$).

N-(2,3,4-Trihydroxybenzyl)-3-(3,4-dihydroxyphenyl)-pronanamide (10)

$^1$H-NMR (400 MHz, CD$_3$OD): δ=6.61 (1H, d, 2.1 Hz), 6.61 (1H, d, 8 Hz), 6.47 (1H, dd, 8.0 Hz, 2.1 Hz), 6.41 (1H, d, 8.3 Hz), 6.28 (1H, d, 8.3 Hz), 4.18 (2H, s), 2.70–2.77 (2H, m), 2.39–2.44 (2H, m) ppm; $^{13}$C-NMR (100 MHz, CD$_3$OD): δ=176.2 (s), 146.7 (s), 146.2 (s), 145.3 (s), 144.6 (s), 134.8 (s), 133.7 (s), 121.0 (d), 120.6 (d), 118.2 (s), 116.5 (d), 116.4 (d), 108.0 (d), 40.1 (t), 39.2 (t), 32.4 (t) ppm.

N-(3,4-Dihydroxybenzyl)-3,4-dihydroxy-E-cinnamamide (11)

Caffeic acid (5 g, 27.8 mmol) is dissolved in pyridine (15 ml) and stirred with acetic anhydride (18 ml) at 100° C. for 1.5 h. The solvents were distilled off and the residue was crystallized from toluene/1,4-dioxane. The purified 3,4-diacetoxy-E-cinnamic acid (2.67 g, 10.4 mmol) was dissolved in 1,4-dioxane (50 ml) here and N-hydroxysuccinimide (1.21 g, 10.5 mmol) and N,N'-dicyclohexylcarbodiimide (2.15 g, 10.4 mmol) were added. After the mixture had been stirred for several hours, the precipitate was filtered off, and the filtrate was evaporated and crystallized using methanol. Yield of N-succinimidyl 3,4-bis(acetyloxy)-E-cinnamate: 2.95 g (79% based on 3,4-di-O-acetylcaffeic acid); $^1$H-NMR (400 MHz, CDCl$_3$): δ=7.85 (1H, d, 15.5 Hz), 7.47 (1H, dd, 8.2 Hz, 2 Hz), 7.42 (1H, d, 2 Hz), 7.28 (1H, d, 8.2 Hz), 6.54 (1H, d, 15.5 Hz), 2.88 (4H, s), 2.13 (3H, 2s), 2.12 (3H, s) ppm.

N-Succinimidyl 3,4-bis(acetyloxy)-E-cinnamate (502 mg, 1.39 mmol) and 3,4-dihy-droxybenzylamine hydrobromide (311 mg, 1.41 mmol) were dissolved in water (10 ml) and 1.4-dioxane (10 ml) under nitrogen. After NaHCO$_3$ (350 mg, 4.16 mmol) had been added, the solution was stirred for 2.5–3 h at about 70° C. and left to cool. The mixture was extracted with ethyl acetate the combined organic phases were washed with hydrochloric acid (10%), water and saturated aqueous NaCl solution, dried over Na$_2$SO$_4$ and filtered, and the filtrate was evaporated under reduced pressure and the residue was purified by chromatography on silica gel. Yield: 254 mg (61%); $^1$H-NMR (400 MHz, CD$_3$OD): δ=7.41 (1H, d, 15.6 Hz), 7.00 (1H, d, 2.1 Hz), 6.90 (1H, ddd, 8.13 Hz, 2.13 Hz, 0.5 Hz), 6.78–6.70 (3H, m), 6.63 (1H, dd, 8.1 Hz, 2.1 Hz), 6.39 (1H, d, 15.6 Hz), 4.32 (2H, s) ppm; $^{13}$C-NMR (100 MHz, CD$_3$OD): δ=169.1 (s), 148.8 (s), 146.8 (s), 146.5 (s), 145.7 (s), 142.4 (d), 131.5 (s), 128.4 (s), 122.1 (d), 120.3 (d), 118.4 (d), 116.5 (d), 116.3 (d), 116.0 (d), 115.1 (d), 44.1 (t) ppm; MS (EI): m/z=301.2 (52%), 179.1 (45%), 178.2 (26%), 163.1 (64%), 138.1 (100%), 135.1 (22%), 134.1 (23%), 123.1 (25%), 89.1 (34%), 77.1 (23%).

Using an analogous method, the following compounds were obtained in the form of colourless, amorphous solids:

N-(4-Hydroxy-3-methoxybenzyl)-3,4-dihydroxy-E-cinnamamide (12)

$^1$H-NMR (400 MHz, CD$_3$OD): δ=7.42 (1H, d, 15.6 Hz), 7.00 (1H, d, 2.4 Hz), 6.91–6.90 (1H, m), 6.90 (1H, ddd, 8 Hz, 2.4 Hz, 0.6 Hz), 6.752 (1H, d, 2 Hz), 6.750 (1H, d, 8 Hz), 6.74 (1H, dd, 8 Hz, 0.6 Hz), 6.39 (1H, d, 15.6 Hz), 4.38 (2H, s), 3.84 (3H, s) ppm; $^{13}$C-NMR (100 MHz, CD$_3$OD): δ=169.1 (s), 149.1 (s), 148.8 (s), 147.0 (s), 146.8 (s), 142.5 (d), 131.5 (s), 128.4 (s), 122.2 (d), 121.6 (d), 118.4 (d), 116.5 (d), 116.2 (d), 115.1 (d), 112.6 (d), 56.4 (q), 44.3 (t) ppm; MS (EI): m/z=315.2 (71%), 164.1 (21%), 163.1 (50%), 153.2 (19%), 152.1 (100%), 137.1 (38%), 136.1 (24%), 135.1 (15%), 89.1 (19%).

N-(3,5-Dimethoxy-4-hydroxybenzyl)-3,4-dihydroxy-E-cinnamamide (13)

$^1$H-NMR (400 MHz, CD$_3$OD): δ=7.43 (1H, d, 15.6 Hz), 7.00 (1H, d, 2.1 Hz), 6.91 (1H, ddd, 8.2 Hz, 2.1 Hz, 0.5 Hz), 6.76 (1H, d, 8.2 Hz), 6.62 (2H, s,), 6.40 (1H, d, 15.6 Hz), 4.38 (2H, s), 3.83 (6H, s) ppm; $^{13}$C-NMR (100 MHz, CD$_3$OD): δ=169.1 (s), 149.4 (s), 148.9 (s), 146.8 (s), 142.6 (d), 135.9 (s), 130.7 (s), 128.3 (2*s), 122.2 (d), 118.3 (d), 116.5 (d), 115.1 (d), 106.2 (2*d), 56.8 (2*q), 44.6 (t) ppm; MS (EI): m/z=345.0 (48%), 183.1 (19%), 182.1 (100%), 179.0 (28%), 178.0 (16%), 167.0 (45%), 163.0 (38%), 140.0 (15%), 135.0 (16%), 89.0 (20%).

N-(2,3,4-Trihydroxybenzyl)-3,4-dihydroxy-E-cinnamamide (14)

$^1$H-NMR (400 MHz, CD$_3$OD): δ=7.41 (1H, d, 15 Hz), 6.90 (1H, d,≈2 Hz), 6.89 (1H, dd, 8 Hz,≈2 Hz), 6.73 (1H, d, 8 Hz), 6.53 (1H, d, 8 Hz), 6.35 (1H, d, 15 Hz), 6.30 (1H, d, 8 Hz), 4.32 ppm (2H, s); MS (ESI pos.) m/z=318.0 (100%, [M+H]$^{30}$), 319.1 (17%, [M+2H]$^+$).

N-(4-Hydroxy-3-methoxybenzyl)-3,4-dihydroxyphenylacetamide (15)

3,4-Dihydroxyphenyl acetic acid (3 g, 17.9 mmol) was dissolved in sodium hydroxide solution (2 mol/l, 26 g) under nitrogen and cooled to −5° C. The methyl chloroformate (3.73 g, 39.3 mmol) was added over the course of 30 min. The mixture was allowed to heat up, was stirred for a further 30 min at room temperature and adjusted to a pH of 3–4 using hydrochloric acid (5%). The product was extracted with ethyl acetate, the organic phase was washed with saturated NaCl solution, dried over $Na_2SO_4$ and filtered, and the filtrate was evaporated under reduced pressure. Yield of 3,4-bis(methoxycarbonyloxy)-phenylacetic acid 5.1 g (quant.). $^1$H-NMR (400 MHz, $d_6$-DMSO): δ=7.34 (1H, d, 8 Hz), 7.30 (1H, d, 2 Hz), 7.23 (1H, dd, 8 Hz, 2 Hz), 3.82 (6H, s), 3.61 (2H, s) ppm; MS (ESI pos.): m/z=301.99 (100%, $[M+NH_4]^{30}$ ). 3,4-Bis(methoxycarbonyloxy)-phenylacetic acid (5 g, 17.6 mmol) and N-hydroxysuccinimide (2.02 g, 17.6 mmol) were dissolved in 1,4-dioxane under nitrogen. N,N-di-cyclohexylcarbodiimide (3.63 g, 17.6 mmol) was added to the solution and the mixture, which was turning cloudy, was stirred for 72 h at room temperature. The mixture is filtered and the filtrate is evaporated under reduced pressure. The residue is purified by chromatography on silica gel using the eluent ethyl acetate. Yield of N-succinimidyl 3,4-bis(methoxycarbonyloxyphenyl)-acetate: 5.94 g (89% of theory). $^1$H-NMR (400 MHz, $d_6$-DMSO): δ=7.45–7.40 (2H, m), 7.33 (1H, dd, 8 Hz, 2 Hz), 4.20 (2H, s), 3.84 (6H, s), 2.81 (4H, s) ppm.

N-Succinimidyl 3,4-bis(methoxycarbonyloxy)-phenylacetate (500 mg, 1.76 mmol) and 4-hydroxy-3-methoxybenzylamine hydrochloride were dissolved in 20 ml of 1,4-dioxane and 20 ml of water under nitrogen, and sodium hydrogencarbonate (148 mg, 1.76 mmol) was added. The mixture was heated at 80° C. for 2 h, treated with further sodium hydrogen carbonate (325 mg, 3.87 mmol), stirred for a further 1 h at 80° C. and left to cool. The orange-red mixture was acidified using hydrochloric acid (5%) and extracted with ethyl acetate. The organic phase was washed with saturated NaCl solution, dried over $Na_2SO_4$ and filtered, and the filtrate was evaporated under reduced pressure. The residue was purified by chromatography on silica gel using the eluent ethyl acetate. Yield of N-(4-hydroxy-3-methoxybenzyl)-3,4-dihydroxyphenylacetamide 340 mg (63% of theory).

$^1$H-NMR (400 MHz, $d_6$-DMSO): δ=8.78 (1H, s), 8.76 (1H, s), 8.66 (1H, s), 8.26 (1H, t, 6 Hz), 6.76–6.59 (5H, m), 6.52 (1H, dd, (Hz, 2Hz), 4.14 (2H, d, 6 Hz), 3.66 (3H, s), 3.24 (2H, s) ppm; MS (ESI pos.) m/z=303.96 (100%, $[M+H]^+$), 606.6 (30%, $[2M+H]^{30}$ ).

Using an analogous method, the compound below was obtained in the form of a colourless, amorphous solid:
N-(3,4-Dihydroxybenzyl)-3,4-dihydroxyphenylacetamide (16)
$^1$H-NMR (400 MHz, $CDCl_3$): δ=6.74–6.65 (4H, m), 6.61–6.54 (2H, m), 4.19 (2H, s), 3.36 (2H, s) ppm; MS (ESI neg.): m/z=288.03 (100%, $[M−H]^−$), 333.58 (17%, $[M−H+HCOOH]^−$), 576.70 (13%, $[2M−H]^−$).

EXPERIMENTS

Activity as Free-radical Scavengers

The activity of example compounds 1 to 16 as free-radical scavengers was compared with that of a traditional free-radical scavenger. The DPPH (1,1-diphenyl-2-picrylhydrazyl) test for the removal of free radicals was used.

DPPH was dissolved in methanol to a concentration of 100 μmol/l. A series of dilutions of the example compounds, vitamin C, α-tocopherol, BHT, ferulic acid and of the naturally occurring N-(2-[4-hydroxyphenyl]ethyl)-4-hydroxy-3-methoxy-E-cinnamamide were prepared in methanol. Methanol was used as the control. 2500 μl of the DPPH solution were mixed with 500 μl of each test solution and the decrease in absorption at 515 nm was read until the decrease was less than 2% per hour. The activity of the test substances as free-radical scavengers was calculated using the following equation:

Activity as free-radical scavenger (%)=100−(absorption of the test compounds)/(absorption of the control)×100.

The activity as free-radical scavengers (%) in a series of dilutions of test compounds was used to calculate, for each test compound, the effective relative concentration $EC_{50}$ (based on the starting concentration of DPPH, EC=c (test compound)/c(DPPH)) of a test compound, at which 50% of the free radical DPPH had been removed. The results are given in Table 1:

TABLE 1

| Test compound | $EC_{50}$/(mol/mol) |
|---|---|
| Example 1 | 0.1 |
| Example 2 | 0.097 |
| Example 3 | 0.097 |
| Example 4 | 0.1 |
| Example 5 | 0.0097 |
| Example 6 | 0.103 |
| Example 7 | 0.094 |
| Example 8 | 0.119 |
| Example 9 | 0.07 |
| Example 10 | 0.069 |
| Example 11 | 0.043 |
| Example 12 | 0.089 |
| Example 13 | 0.1 |
| Example 14 | 0.054 |
| Example 15 | 0.105 |
| Example 16 | 0.053 |
| N-(2-[4-hydroxyphenyl]-ethyl-4-hydroxy-3-methoxy-E-cinnamamide | 0.441 |
| Vitamin C | 0.270 |
| α-Tocopherol | 0.250 |
| Ferulic acid | 0.350 |
| BHT | 0.240 |

Activity as Antioxidants

The activity of example compounds 1 to 16 as antioxidants was compared with that of traditional antioxidants. The test system used was the accelerated autoxidation of lipids by air with or without antioxidant using a RANCIMAT apparatus (RANCIMAT is a registered trade mark of Metrohm AG, Herisau, Switzerland).

The example compounds, vitamin C, α-tocopherol, BHT, ferulic acid and the naturally occurring N-(2-[4-hydroxyphenyl]-ethyl)-4-hydroxy-3-methoxy-E-cinnamamide were dissolved in methanol or acetone, and 100 μl of each test solution were added to a 3 g pre-prepared oil sample (soy bean oil, purified over alumina type N). In a control sample, only solvent was added. A constant, dry air stream (20 l/h) was blown through the oil sample, which contained the test solution and was heated to 100° C., and the volatile oxidation products (predominantly short-chain fatty acids such as formic or acetic acid) were collected in a receiver containing water. The conductivity of this aqueous solution was continuously measured and recorded. The oxidation of (unsaturated) fats proceeds only very slowly for some time and then suddenly increases. The time to the increase is referred to as the induction period (IP).

The following equation was used to calculate the antioxidative index (AOI):

$$AOI=IP_{(with\ test\ solution)}/IP_{(control\ sample)}$$

The results are given in Table 2:

TABLE 2

| Test compound | AOI with 0.05% of test substance |
|---|---|
| Example 1 | 11.41 |
| Example 2 | 7.58 |
| Example 3 | 11.7 |
| Example 4 | 17.3 |
| Example 5 | 21.4 |
| Example 6 | 13.9 |
| Example 7 | 7.7 |
| Example 8 | 13.2 |
| Example 9 | 19.8 |
| Example 10 | 24.6 |
| Example 11 | 14.9 |
| Example 12 | 14.3 |
| Example 13 | 3.6 |
| Example 14 | 27.5 |
| Example 15 | 7.84 |
| Example 16 | 8.84 |
| N-(2-[4-hydroxyphenyl-ethyl)4-hydroxy-3-methoxy-E-cinnamamide | 1.41 |
| Vitamin C | 1.17 |
| α-Tocopherol | 5.05 |
| Ferulic acid | 1.79 |
| BHT | 4.77 |

What is claimed is:

1. A compound of the formula (I):

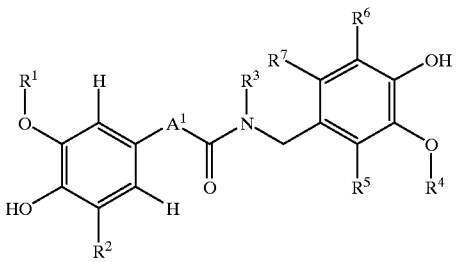

wherein $A^1$ is $CH_2$, and $R^1$ is hydrogen or $C_{1-4}$ alkyl, and $R^2$ is hydrogen or $-O-R^8$, in which $R^8$ is hydrogen or $C_{1-4}$ alkyl, and $R^3$ is hydrogen, $C_{1-22}$ acyl, $C_{1-22}$ alkyl, $C_{1-22}$ alkenyl, or $-(CH_2-CH_2-O-)_{1-15}H$, and $R^4$ is hydrogen or $C_{1-4}$ alkyl, and wherein in at least one of $R^1$ or $R^4$ is hydrogen, and $R^5$ is hydrogen or $-O-R^9$, in which $R^9$ is hydrogen or $C_{1-4}$ alkyl, and $R^1$ is hydrogen or $-O-R^9$, in which $R^9$ is hydrogen or $C_{1-4}$ alkyl, and $R^1$ is hydrogen or $-O-R^9$, in which $R^9$ is hydrogen or $C_{1-4}$ alkyl.

2. A compound selected from the group consisting of:

N-(3,4-dihydroxybenzyl)-3,5-dimethoxy-4-hydroxy-E-cinnamamide,

N-(2,3,4-trihydroxybenzyl)-4-hydroxy-3-methoxy-E-cinnamamide,

N-(2,3,4-trihydroxybenzyl)-3,5-dimethoxy-4-hydroxy-E-cinnamamide,

N-(3,4,5-trihydroxybenzyl)-4-hydroxy-3-methoxy-E-cinnamamide,

N-(3,4-dihydroxybenzyl)-4-hydroxy-3-methoxyphenylacetamide,

N-(3,4-dihydroxybenzyl)-3-(4-hydroxy-3-methoxyphenyl)-propanamide,

N-(4-hydroxy-3-methoxybenzyl)-3-(3,4-dihydroxyphenyl)-propanamide,

N-(2,3,4-trihydroxybenzyl)-3-(3,4-dihydroxyphenyl)-propanamide,

N-(4-hydroxy-3-methoxybenzyl)-3,4-dihydroxy-E-cinnamamide,

N-(3,5-deimethoxy-4-hydroxybenzyl)-3,4-dihydroxy-E-cinnamamide,

N-(2,3,4-trihydroxybenzyl)-3,4-dihydroxy-E-cinnamamide,

N-(4-hydroxy-3-methoxybenzyl)-3,4-dihydroxyphenylacetamide, and

N-(3,4-dihydroxybenzyl)-3,4-dihydroxyphenylacetamide.

3. A method of preparing a compound of formula (I):

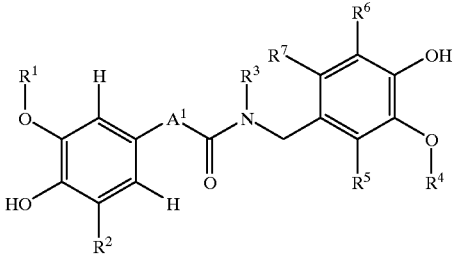

wherein $A^1$ is $CH_2$ and $R^1$ is hydrogen or $C_{1-4}$ alkyl, and $R^2$ is hydrogen or $-O-R^8$, in which $R^8$ is hydrogen or $C_{1-4}$ alkyl, and $R^3$ is hydrogen, $C_{1-22}$ acyl, $C_{1-22}$ alkyl, $C_{1-22}$ alkenyl, or $-(CH_2-CH_2-O-)_{1-15}H$, and $R^4$ is hydrogen or $C_{1-4}$ alkyl, and wherein in at least one of $R^1$ or $R^4$ is hydrogen, and $R^5$ is hydrogen or $-O-R^9$, in which $R^9$ is hydrogen or $C_{1-4}$ alkyl, and $R^6$ is hydrogen or $-O-R^9$, in which $R^9$ is hydrogen or $C_{1-4}$ alkyl, and $R^7$ is hydrogen or $-O-R^9$, in which $R^9$ is hydrogen or $C_{1-4}$ alkyl, comprising reacting an activated phenolic acid with a hydroxy-substituted benzylamine.

4. The method of claim 3 wherein the activated phenolic acid is in the form of an acid chloride, an acid anhydride, or an acid ester of an unsubstituted or substituted phenol, N-hydroxysuccinimide or N-hydroxybenzotriazole.

5. The method of claim 3 wherein the activated phenolic acid is protected on the phenolic OH group by a protective group, and the method comprises the further step of cleaving off the protective group.

6. The method of claim 5 where in the protective group is selected from the group consisting of acyl, carbamate, acetyl, benzoyl, methoxycarbonyl, tertbutoxy carbonyl, allyl, and benzyl.

7. The method of claim 3 which is carried out in the presence of a solvent and an auxiliary base.

8. The method of claim 7 wherein the solvent is selected from the group consisting of water, acetone, dioxane, dimethylformamide, tetrahydrofuran, ethyl acetate, and chloroform, and mixtures thereof.

9. The method of claim 7 wherein the auxiliary base is selected from the group consisting of carbonate, hydrogencarbonate, and an hydroxide of ammonium, an alkali metal, an alkaline earth metal, and a tertiary amine.

10. The method of claim 3 wherein the activated phenolic acid is in free form, the hydroxy-substituted benzyl amine is in free form, and a condensing agent is present.

11. The method of claim 10 wherein the condensing agent is a carbodiimide.

12. The method of claim 11 wherein the carbodiimide is N,N'-dicyclohexylcarbodiimide.

13. The method of claim 3 wherein the activated phenolic acid is in the ester form and is selected from the group consisting of N-succinimidyl 4-hydroxy-3-methoxy-E-cinnamate, N-succinimidyl 3,5-dimethoxy-4-hydroxy-E-cinnamate, N-succinimidyl 3,4-bis(acetyloxy-E-cinnamate, N-succinimidyl 3,4-bis(methoxycarbonyloxy)-E-cinnamate, N-succinimidyl 4-hydroxy-3-methoxy-phenylacetate, N-succinimidyl 3-(4-hydroxy-3-methoxyphenyl)-propanoate and N-succinimidyl 3-(3,4-dihydroxyphenyl)-propanoate.

14. The method of claim 3 wherein the hydroxy-substituted benzylamine is selected from the group consisting of 3,4-dihydroxybenzylamine, 4-hydroxy-3-methoxybenzylamine, 3,4-dimethoxy-4-hydroxybenzylamine, 2,3,4-trihydroxybenzylamine, and 3,4,5-trihydroxybenzylamine, and the corresponding ammonium salts.

15. An antioxidant comprising a carrier, and a compound of the formula (I):

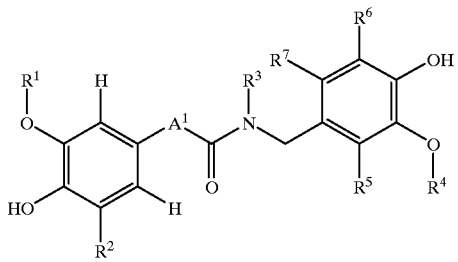

wherein $A^1$ is $CH_2$ and $R^1$ is hydrogen or $C_{1-4}$ alkyl, and $R^2$ is hydrogen or —O—$R^8$, in which $R^8$ is hydrogen or $C_{1-4}$ alkyl, and $R^3$ is hydrogen, $C_{1-22}$ acyl, $C_{1-22}$ alkyl, $C_{1-22}$ alkenyl, or —($CH_2$—$CH_2$—O—)$_{1-15}$H, and $R^4$ is hydrogen or $C_{1-4}$ alkyl, and wherein in at least one of $R^1$ or $R^4$ is hydrogen, and $R^5$ is hydrogen or —O—$R^9$, in which $R^9$ is hydrogen or $C_{1-4}$ alkyl, and $R^6$ is hydrogen or —O—$R^9$, in which $R^9$ is hydrogen or $C_{1-4}$ alkyl, and $R^7$ is hydrogen or —O—$R^9$, in which $R^9$ is hydrogen or $C_{1-4}$ alkyl.

16. The antioxidant of claim 15 wherein the carrier is food.

17. A free-radical scavenger comprising a carrier and a compound of the formula (I):

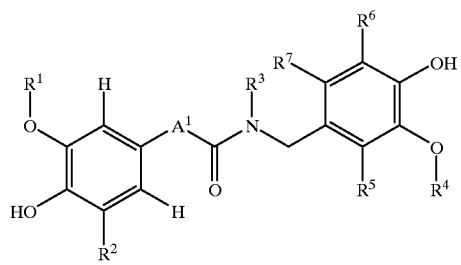

wherein $A^1$ is $CH_2$ and $R^1$ is hydrogen and $R^2$ is hydrogen or —O—$R^8$, in which $R^8$ is hydrogen or $C_{1-4}$ alkyl, and $R^3$ is hydrogen, $C_{1-22}$ acyl, $C_{1-22}$ alkyl, $C_{1-22}$ alkenyl, or —($CH_2$—$CH_2$—O—)$_{1-15}$H, and $R^4$ is hydrogen or $C_{1-4}$ alkyl, and wherein in at least one of $R^1$ or $R^4$ is hydrogen, and $R^5$ is hydrogen or —O—$R^9$, in which $R^9$ is hydrogen or $C_{1-4}$ alkyl, and $R^6$ is hydrogen or —O—$R^9$, in which $R^9$ is hydrogen or $C_{1-4}$ alkyl, and $R^7$ is hydrogen or —O—$R^9$, in which $R^9$ is hydrogen or $C_{1-4}$ alkyl.

18. The free-radical scavenger of claim 17 wherein the carrier is food.

19. A composition comprising a carrier and a compound of the formula (I):

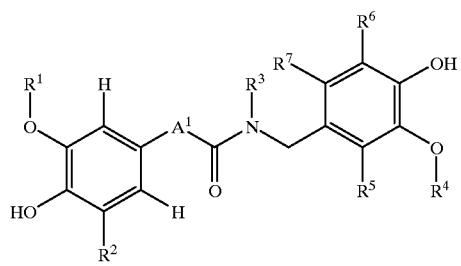

wherein $A^1$ is $CH_2$ and $R^1$ is hydrogen or $C_{1-4}$ alkyl, and $R^2$ is hydrogen or —O—$R^8$, in which $R^8$ is hydrogen or $C_{1-4}$ alkyl, and $R^3$ is hydrogen, $C_{1-22}$ acyl, $C_{1-22}$ alkyl, $C_{1-22}$ alkenyl, or —($CH_2$—$CH_2$—O—)$_{1-15}$H, and $R^4$ is hydrogen or $C_{1-4}$ alkyl, and wherein in at least one of $R^1$ or $R^4$ is hydrogen, and $R^5$ is hydrogen or —O—$R^9$, in which $R^9$ is hydrogen or $C_{1-4}$ alkyl, and $R^6$ is hydrogen or —O—$R^9$, in which $R^9$ is hydrogen or $C_{1-4}$ alkyl, and $R^7$ is hydrogen or —O—$R^9$, in which $R^9$ is hydrogen or $C_{1-4}$ alkyl, wherein the compound is present in an amount effective to improve the efficacy of the composition for protecting and treating hair or skin against the presence of oxidants and free radicals.

20. The composition of claim 19 wherein the composition is in pharmaceutical or cosmetic foam.

21. A compound of the formula (I):

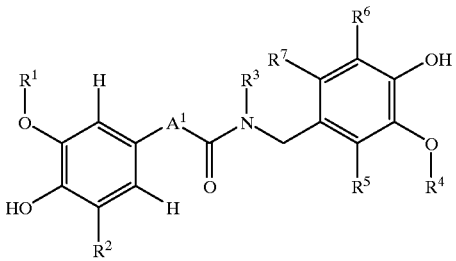

wherein
- $A^1$ is $CH_2$—$CH_2$, and
- $R^1$ is hydrogen or $C_{1-4}$ alkyl, and
- $R^2$ is hydrogen or —O—$R^8$, in which $R^8$ is hydrogen or $C_{1-4}$ alkyl, and
- $R^3$ is hydrogen, $C_{1-22}$ acyl, $C_{1-22}$ alkyl, $C_{1-22}$ alkenyl, or —$(CH_2$—$CH_2$—$O$—$)_{1-15}H$, and
- $R^4$ is hydrogen or $C_{1-4}$ alkyl, and
- wherein in only one of $R^1$ or $R^4$ is hydrogen, and
- $R^5$ is hydrogen or —O—$R^9$, in which $R^9$ is hydrogen or $C_{1-4}$ alkyl, and
- $R^6$ is hydrogen or —O—$R^9$, in which $R^9$ is hydrogen or $C_{1-4}$ alkyl, and
- $R^7$ is hydrogen or —O—$R^9$, in which $R^9$ is hydrogen or $C_{1-4}$ alkyl,
- wherein the compound is present in an amount effective to improve the efficacy of the composition for protecting and treating hair or skin against the presence of oxidants and free radicals.

22. A composition comprising a carrier and the compound of claim 21, wherein the composition has antioxidant activity.

23. A compound of the formula (I):

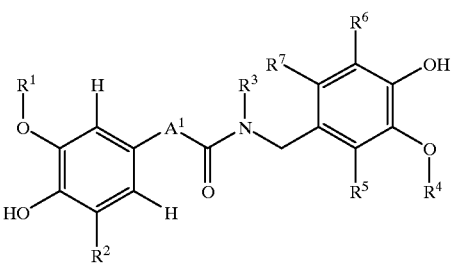

wherein
- $A_1$ is —CH=CH—, and
- $R^1$ is hydrogen, and
- $R^2$ is hydrogen or —O—$R^8$, in which $R^8$ is hydrogen or $C_{1-4}$ alkyl, and
- $R^3$ is hydrogen, $C_{1-22}$ acyl, $C_{1-22}$ alkyl, $C_{1-22}$ alkenyl, or —$(CH_2$—$CH_2$—$O$—$)_{1-15}H$, and
- $R^4$ is $C_{1-4}$ alkyl, and
- $R^5$ is hydrogen or —O—$R^9$, in which $R^9$ is hydrogen or $C_{1-4}$ alkyl, and
- $R^6$ is hydrogen or —O—$R^9$, in which $R^9$ is hydrogen or $C_{1-4}$ alkyl, and
- $R^7$ is hydrogen or —O—$R^9$, in which $R^9$ is hydrogen or $C_{1-4}$ alkyl.

24. A composition comprising a carrier and the compound of claim 23, wherein the composition has antioxidant activity.

* * * * *

UNITED STATES PATENT AND TRADEMARK OFFICE
CERTIFICATE OF CORRECTION

PATENT NO. : 6,117,365
DATED : September 12, 2000
INVENTOR(S) : Jakob Ley

It is certified that error appears in the above-identified patent and that said Letters Patent is hereby corrected as shown below:

Title page,
Column 1,
Lines 18-21, under "OTHER PUBLICATIONS" delete "Halliwell et al., "Free Radicals and Antioxidants in Food and In Vivo: What They Do and How They Work," Critical Reviews in Food Science and Nutrition, vol. 35, (1 and 2), pp. 7-20, (1995)."

Column 2,
Line 17, change "Phytochemnistry," to -- Phytochemistry, --.

Claim 1,
Line 25, (after the line starting with "$R^5$ is hydrogen"), change "$R^1$" to -- $R^6$ --.
Line 26, change "$R^1$" to -- $R^7$ --.

Claim 17,
Line 17, change "$A^1$ is $CH_2$ and" to -- $A^1$ is $CH_2$, and --.

Signed and Sealed this

Eighteenth Day of December, 2001

Attest:

JAMES E. ROGAN
*Attesting Officer*   *Director of the United States Patent and Trademark Office*